(12) United States Patent
Stevens

(10) Patent No.: US 8,469,958 B2
(45) Date of Patent: Jun. 25, 2013

(54) FIXING BLOCK AND METHOD FOR STABILIZING BONE

(75) Inventor: Peter M. Stevens, Salt Lake City, UT (US)

(73) Assignee: Morphographics, LC, Salt Lake City, UT (US)

( * ) Notice: Subject to any disclaimer, the term of this patent is extended or adjusted under 35 U.S.C. 154(b) by 1596 days.

(21) Appl. No.: 11/346,924

(22) Filed: Feb. 3, 2006

(65) Prior Publication Data

US 2006/0184169 A1 Aug. 17, 2006

Related U.S. Application Data

(60) Provisional application No. 60/653,222, filed on Feb. 15, 2005.

(51) Int. Cl.
*A61B 17/60* (2006.01)
*A61B 17/62* (2006.01)

(52) U.S. Cl.
USPC .............................................. 606/56; 606/59

(58) Field of Classification Search
USPC ......... 606/53–56, 59, 86 R, 90, 96, 104–105, 606/151, 250, 260, 278, 329; 403/394, 362, 403/324–325
See application file for complete search history.

(56) References Cited

U.S. PATENT DOCUMENTS

| | | | | | |
|---|---|---|---|---|---|
| 3,436,047 | A | * | 4/1969 | Foltz | 248/317 |
| 4,098,269 | A | * | 7/1978 | Judet | 606/54 |
| 4,258,708 | A | * | 3/1981 | Gentile | 606/57 |
| 4,548,199 | A | * | 10/1985 | Agee | 606/57 |
| 4,889,111 | A | * | 12/1989 | Ben-Dov | 606/56 |
| 5,393,161 | A | * | 2/1995 | Mata et al. | 403/133 |
| 5,443,464 | A | * | 8/1995 | Russell et al. | 606/54 |
| 5,728,095 | A | * | 3/1998 | Taylor et al. | 606/54 |
| 5,728,096 | A | * | 3/1998 | Faccioli et al. | 606/54 |
| 5,885,282 | A | * | 3/1999 | Szabo | 606/56 |
| 6,129,727 | A | * | 10/2000 | Austin et al. | 606/56 |
| 6,235,062 | B1 | * | 5/2001 | Gramnas | 623/33 |
| 6,280,133 | B1 | * | 8/2001 | Haberle | 411/392 |
| 2004/0073212 | A1 | * | 4/2004 | Kim | 606/56 |

* cited by examiner

*Primary Examiner* — Nicholas Woodall
*Assistant Examiner* — Larry E Waggle, Jr.
(74) *Attorney, Agent, or Firm* — Workman Nydegger

(57) ABSTRACT

A system is provided for stabilizing bone. The system includes a fixing block, a pin having a far end which is adapted to be fixed directly into bone and a near end which enters the fixing block, and a frame on which the fixing block is fixable. The pin enters the fixing block in a non-orthogonal manner in order to permit the pin to enter the bone with an orientation which is non-orthogonal to the bone's surface, thereby permitting the pin to engage more of the bone.

26 Claims, 16 Drawing Sheets

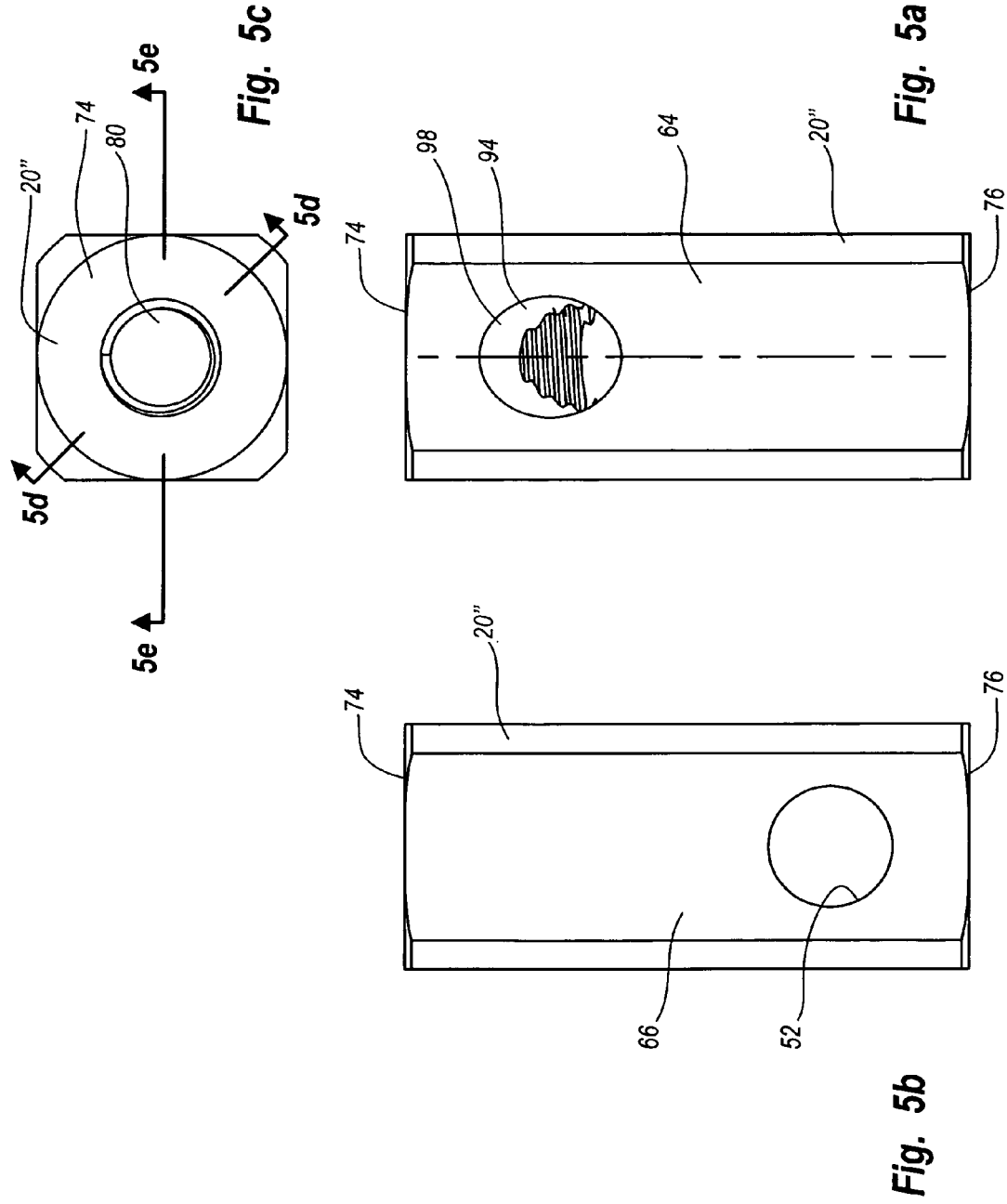

FIXING BLOCK AND METHOD FOR STABILIZING BONE

CROSS-REFERENCE TO RELATED APPLICATIONS

This application claims the benefit of U.S. Provisional Application Ser. No. 60/653,222, filed on Feb. 15, 2005, entitled SYSTEM AND METHOD FOR STABILIZING BONE, which is incorporated herein in its entirety by reference.

BACKGROUND OF THE INVENTION

1. The Field of the Invention

This invention relates to fixators. In particular, this invention relates to external fixators (frames) commonly employed for the orthopedic stabilization of long bones during fracture management or deformity correction.

2. The Relevant Technology

Bone fixators have existed for many years. In a simple embodiment, fixators are plates which span a fissure, fracture or surgically divided bone in order to hold each bone portion in a proper relative position for healing.

In more complex conceptions, such as the Ilizarov type fixator, an external frame is used, together with pins, called "half-pins", which enter the opposing ends of the bone, in order to stabilize the bone by virtue of the rigid, external frame to which the pins are fixed.

Standard half pins employed for fixation of long bone fragments are typically threaded to engage both sides of the bone and prevent slippage. Prior to insertion, a hole must first be drilled in the bone. The drill bit is then removed and the half pin inserted. The technique requires the placement of multiple threaded pins through bone fragments. These pins then are anchored to external bars or rings. When desired, the position of the frame may subsequently be adjusted to correct deformities or to gain limb length. The success of this technique is predicated upon a secure interface between each of the pins and the adjacent bone. If one or more pins loosen, stability will be lost and the result may be compromised. Suboptimal pin placement may result in pin loosening or breakage or stress fracture of the bone requiring secondary surgery.

External fixators have become ubiquitous in orthopedic trauma and reconstructive surgery. Despite the wide variety of fixators on the market, the common denominator requires the placement of half pins transversely through both sides (cortices) of the bone. These pins are then clamped to the external ring or bar fixators. It is commonplace to apply three pins per bone segment in order to adequately preserve alignment and bone stability. Transverse pins have the potential disadvantage of being subject to failure due to the considerable and repetitive bending stresses imparted by muscle contraction and by the forces of weight bearing. As a result, the pin/bone interface may become unstable; infection or pin breakage may ensue. Furthermore pins may need to be applied at a considerable distance from the rings. This requires the construction of a somewhat unwieldy and weighty superstructure in order to adequately secure the pins.

What is needed therefore is a device which permits more secure and versatile fixation of the bone fragments.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 5a is an elevated back side view of the fixing block shown in FIG. 4;

FIG. 5b is an elevated side view of the fixing block shown in FIG. 4;

FIG. 5c is a top plan view of the fixing block shown in FIG. 4;

DETAILED DESCRIPTION OF THE PREFERRED EMBODIMENTS

Figure 1A:
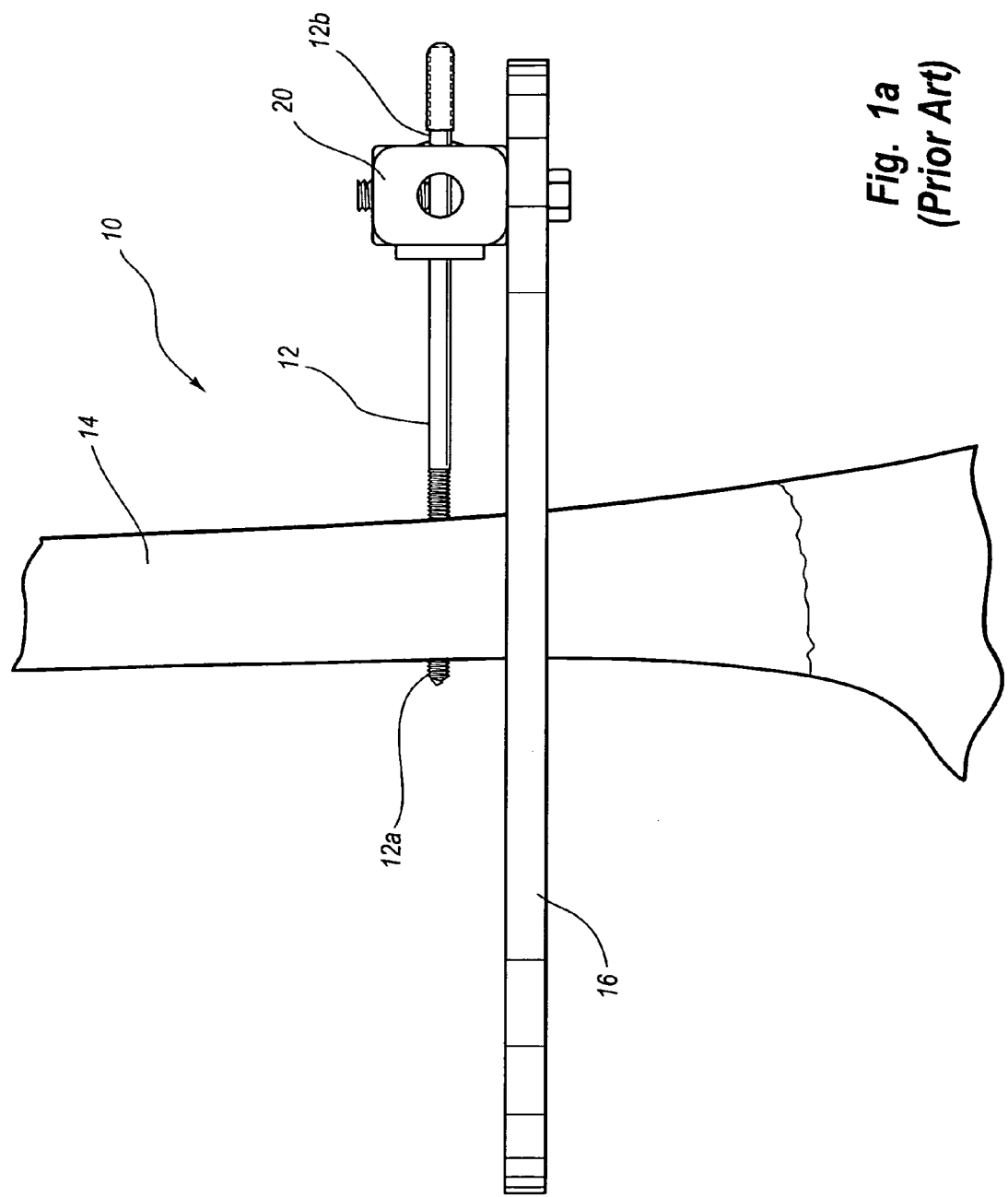
FIG. 1a is a schematic diagram of the standard practice of drilling a transverse pin across a bone and clamping it onto an external frame.
Figure 1B:
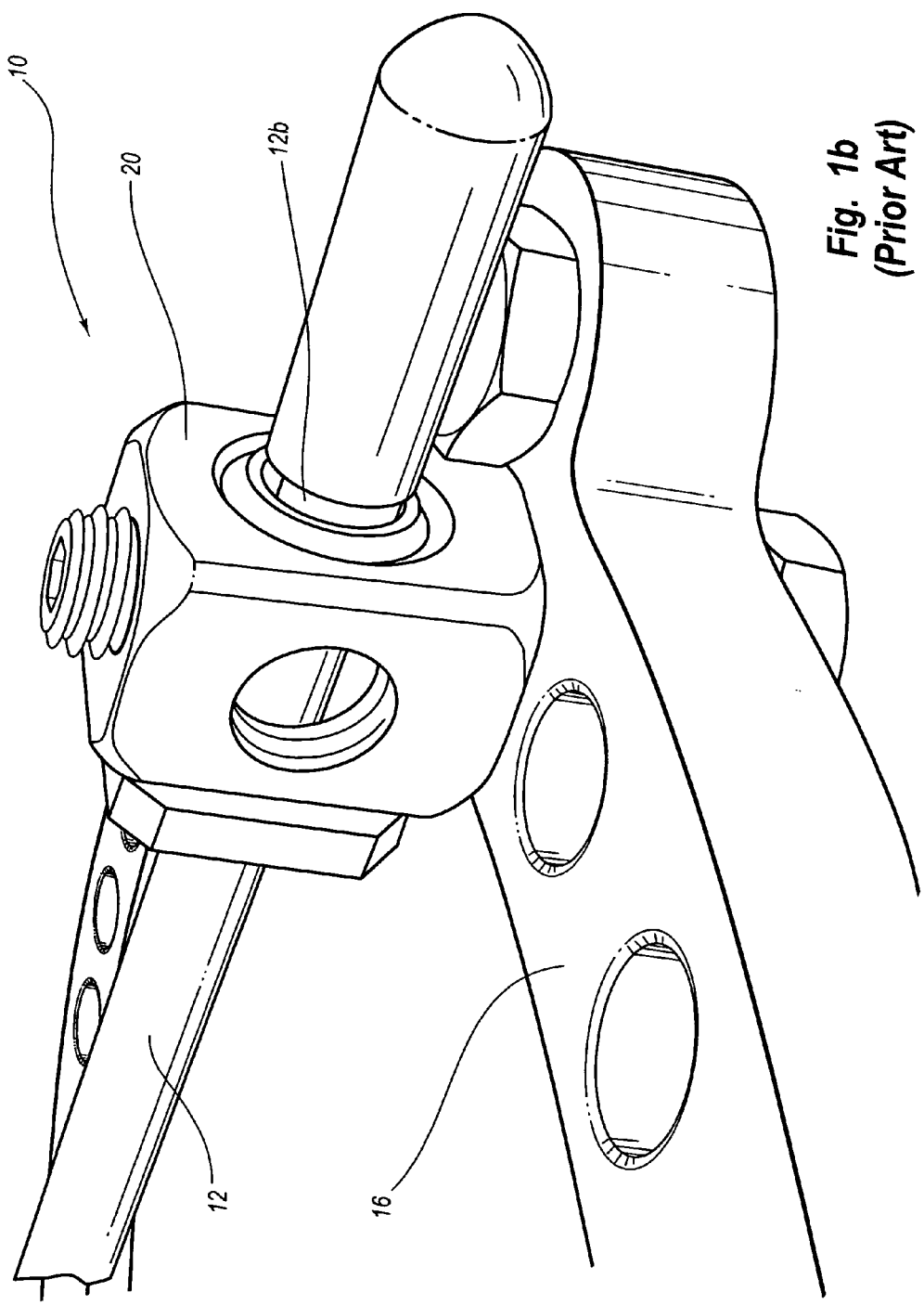
FIG. 1b is a perspective view showing the transverse pin fixation of the prior art.

Referring now to FIGS. 1a and 1b, a bone stabilizing system 10 of the prior art is shown. The system 10 is used to transversely drill a bone pin 12 across the bone 14 and clamp it onto the external frame 16. The system 10 includes a fixing block 20, the bone pin 12 having a distal end 12a which is adapted to be fixed directly into bone 14 and a proximal end 12b which enters the fixing block 20, and the frame 16 on which the fixing block 20 is fixable. The bone pin 12 enters the fixing block 20 in an orthogonal manner.

Figure 2A:
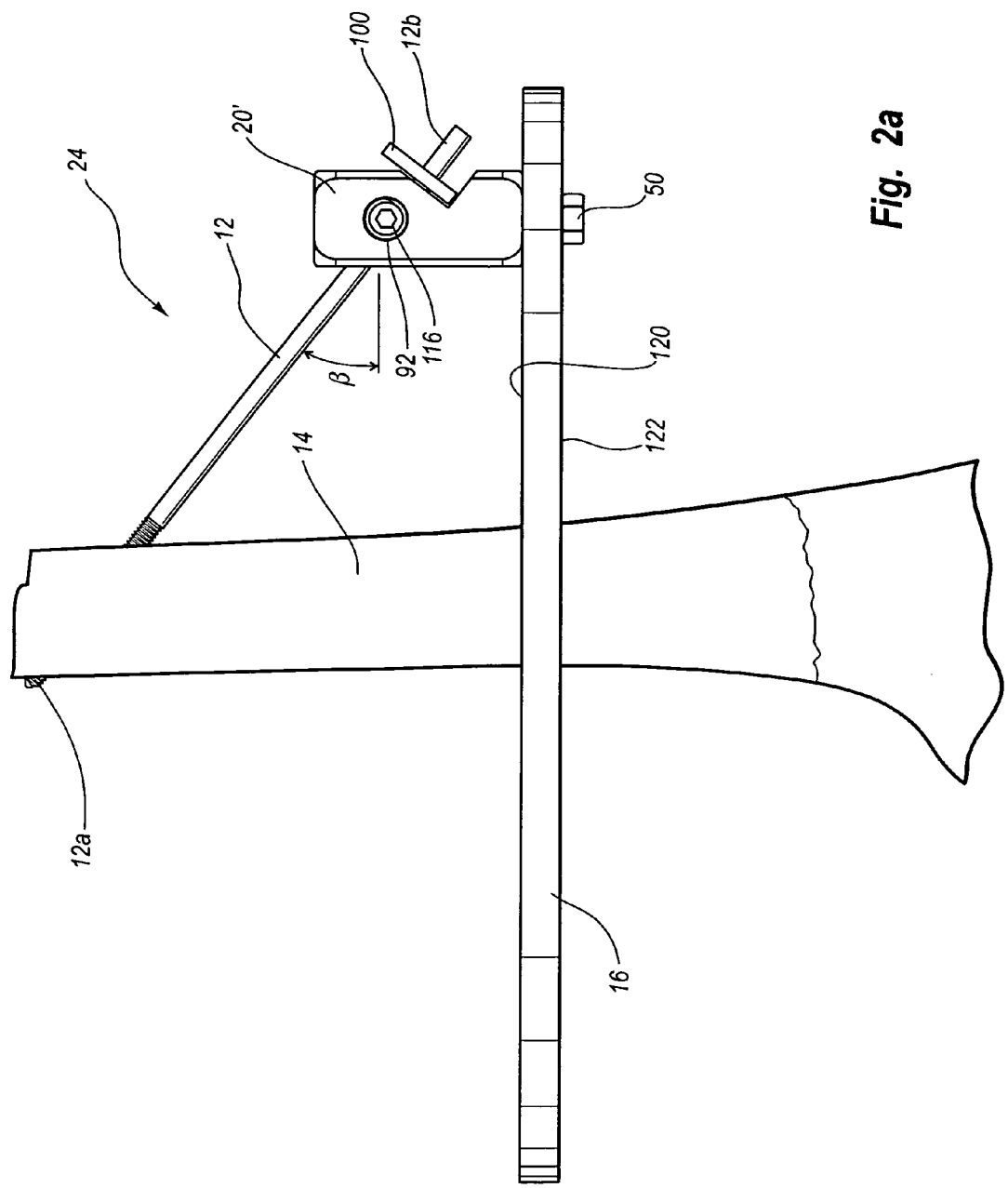
FIG. 2a is a perspective view of one embodiment of the invention wherein placement of the bone pin into the bone at an angle is shown.
Figure 2B:
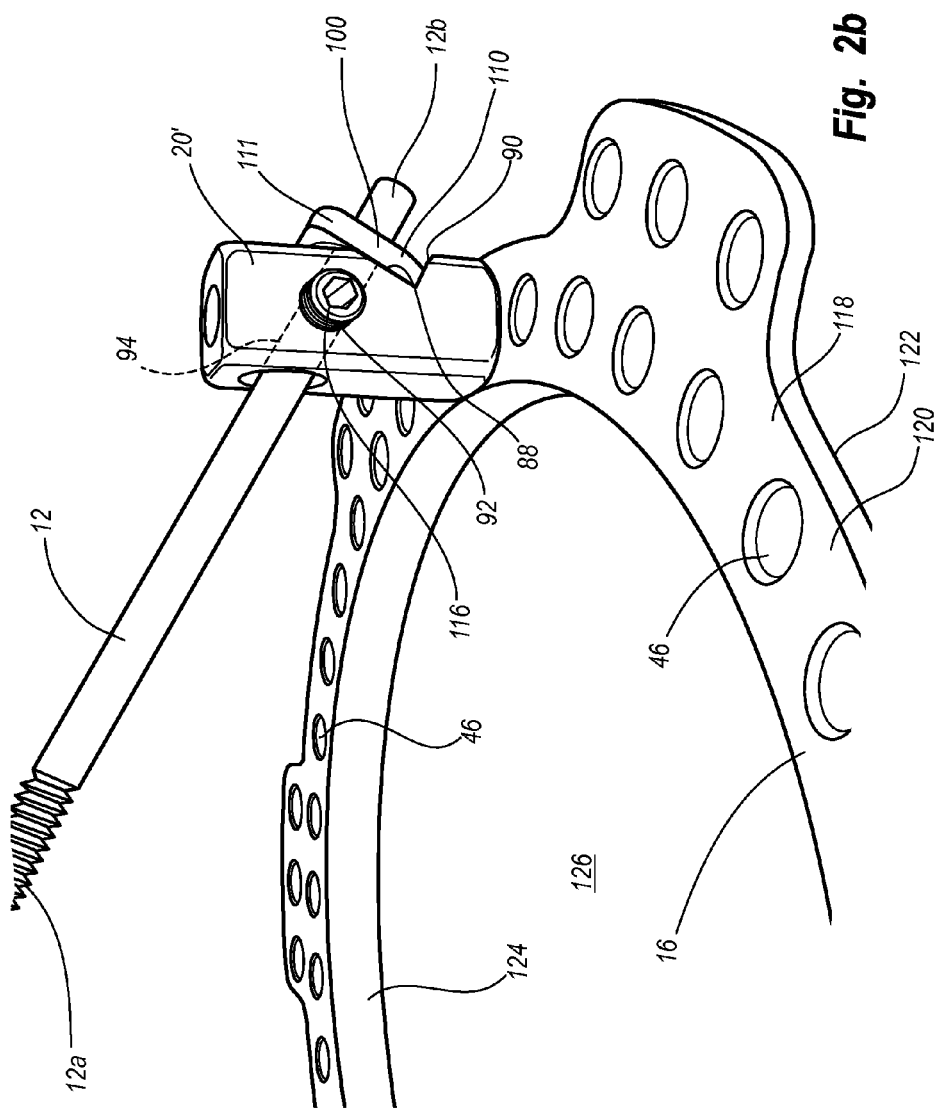
FIG. 2b is a perspective view of the system shown in FIG. 2a showing attachment to a frame.

Depicted in FIGS. 2a and 2b is one embodiment of an inventive bone stabilizing system 24 incorporating features of the present invention. System 24 includes a fixing block 20', the bone pin 12, and the frame 16 on which the fixing block 20' is removably fixed. The bone pin 12 enters the fixing block 20' in a non-orthogonal manner in order to permit the bone pin 12 to enter the bone 14 with an orientation which is non-orthogonal to the bone's surface, thereby permitting the bone pin 12 to engage more of the bone 14.

Figure 2C:
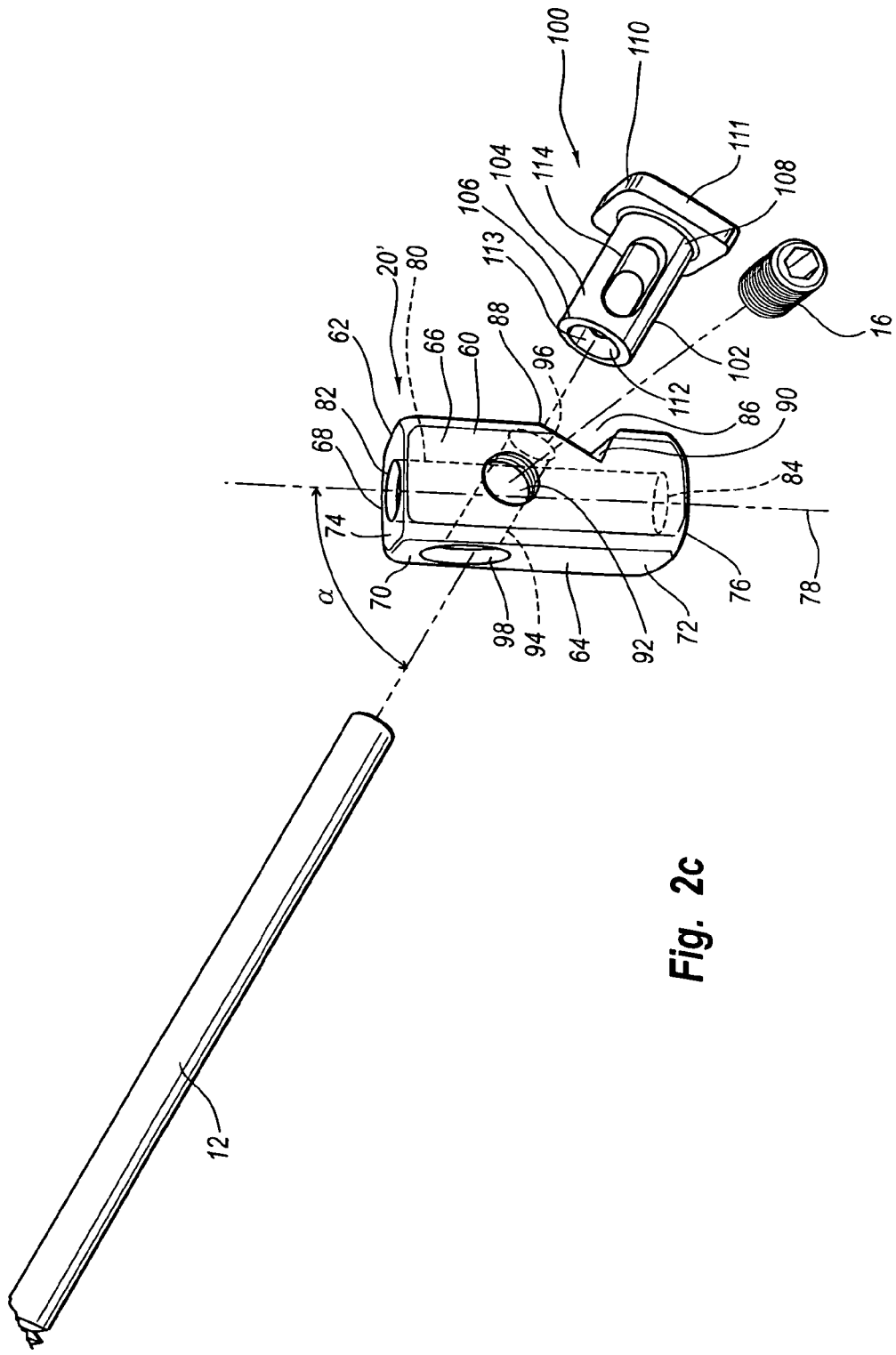
FIG. 2c is an exploded view of the system shown in FIG. 2b.

More specifically, as depicted in FIG. 2c, fixing block 20' comprises a body 60 having a front face 62 and an opposing back face 64 and also a first side 66 and an opposing second side 68 that each extend between a first end 70 and an opposing second end 72. First end 70 terminates at a first end face 74 while second end 72 terminates at a second end face 76. In the embodiment depicted, body 60 has a substantially parallel piped configuration having a substantially square or rectangular transverse cross section. As such, opposing faces 62 and 64 are substantially planer and are disposed in substantially parallel alignment. Similarly, opposing sides 66 and 68 and opposing end faces 74 and 76 are substantially planer and are disposed in substantially parallel alignment to each other. In alternative embodiments, however, body 60 can have a variety of alternative transverse cross sectional configurations including circular or other polygonal or irregular configurations.

A central longitudinal axis 78 extends between opposing end faces 74 and 76. In the depicted embodiment, a mounting channel 80 extends along axis 78 between opposing end faces 74 and 76. Mounting channel 80 terminates at a first opening 82 formed on first end face 74 and a second opening 84 formed on second end face 76. All or portions of an interior surface of mounting channel 80 can be threaded so that a fastener can be advanced into first opening 82 or second opening 84 and threadedly engage with body 60. In alternative embodiments mounting channel 80 need not extend all the way through body 60. Rather, a first mounting channel can be formed on first end face 74 and/or a second mounting channel can be formed on second end face 76 wherein the first and second mounting channels need not connect. That is, the mounting channels can comprise blind sockets.

An optional notch 86 is formed on front face 62. Notch 86 is bounded by an engagement face 88 and a support face 90 that are each substantially planer and extend between opposing side faces 66 and 68. Faces 88 and 90 typically intersect at an orthogonal angle although other orientations can also be used. A placement channel 94 extends between a first opening 96 formed on engagement face 88 and a second opening 98 formed on back face 64. Engagement face 88 and placement channel 94 are typically oriented such that placement channel 94 intersects orthogonally with engagement face 88. Furthermore, placement channel 94 intersects with axis 78 and/or mounting channel 80 at an inside angle α that is an oblique angle. The angle α is typically in a range between about 15° to about 75° with about 60° to about 30° being more common and about 50° to about 40° being still more common. Other angles can also be used. As will be discussed below in greater detail, an access port 92 is formed on first side 66 and communicates with placement channel 94.

A guide sleeve 100 is also depicted in FIG. 2c. Guide sleeve 100 comprises a tubular sleeve 102 having an exterior surface 104 extending between a distal end 106 and an opposing proximal end 108. An enlarged head 110 is formed at proximal end 108. Head 110 has a perimeter edge 111 having a substantially rectangular, square, or other polygonal configuration. Guide sleeve 100 has an interior surface 113 that bounds a passageway 112 longitudinally extending through sleeve 102 and head 110. A transition port 114 transversely extends through sleeve 102 at a location between opposing ends of sleeve 102 so as to intersect with passageway 112.

During use, as depicted in FIGS. 2b and 2c, sleeve 102 is received within first opening 96 of placement channel 94 and advanced therein until head 110 is disposed adjacent to engagement face 88. In this position, transition port 114 is aligned with access port 92 and perimeter edge 111 of head 110 is disposed adjacent to support face 90. As a result of the polygonal configuration of head 110, support face 90 prevents unwanted rotation of guide sleeve 100 within placement channel 94. Once guide sleeve 100 is positioned, bone pin 12 is selectively advanced through passageway 112 of guide sleeve 100 and placement channel 94 of body 60. Bone pin 12 is secured to bone 14 at the desired location and orientation either before or after passing bone pin 12 through fixing block 20'. A fastener 116, such as a set screw, bolt, or other type fastener, is then threaded into access port 92 so as to pass through transition port 114 and engage directly against bone pin 12. Fastener 116 thus securely engages bone pin 12 to fixing block 20'. It is appreciated that bone pin 12 is disposed at the same orientation as placement channel 94 so that bone pin 12 intersects with axis 78, mounting channel 80 and back face 64 at the oblique angle α.

In part, guide sleeve 100 functions so that a variety of bone pins 12 having different sizes and/or configurations can be used with the same fixing block 20'. For example, sleeve 102 of guide sleeve 100 has exterior surface 104 that is substantially complementary to the interior surface of placement channel 94 and has interior surface 113 that is substantially complementary to the exterior surface of bone pin 12. As a result, by using guide sleeve 100 within placement channel 94 a close tolerance fit can be formed between bone pin 12 and fixing block 20'. For smaller or larger bone pins 12, alternative guide sleeves 100 can be used which are configured to fit in close tolerance with the corresponding bone pins. Accordingly, by using a variety of different guide sleeves 100, a variety of different bone pins can be used with fixing block 20' while still maintaining a close tolerance fit with fixing block 20'. As will be discussed below in alternative embodiments, it is appreciated that guide sleeve 100 and notch 86 can be eliminated.

Figure 3A:
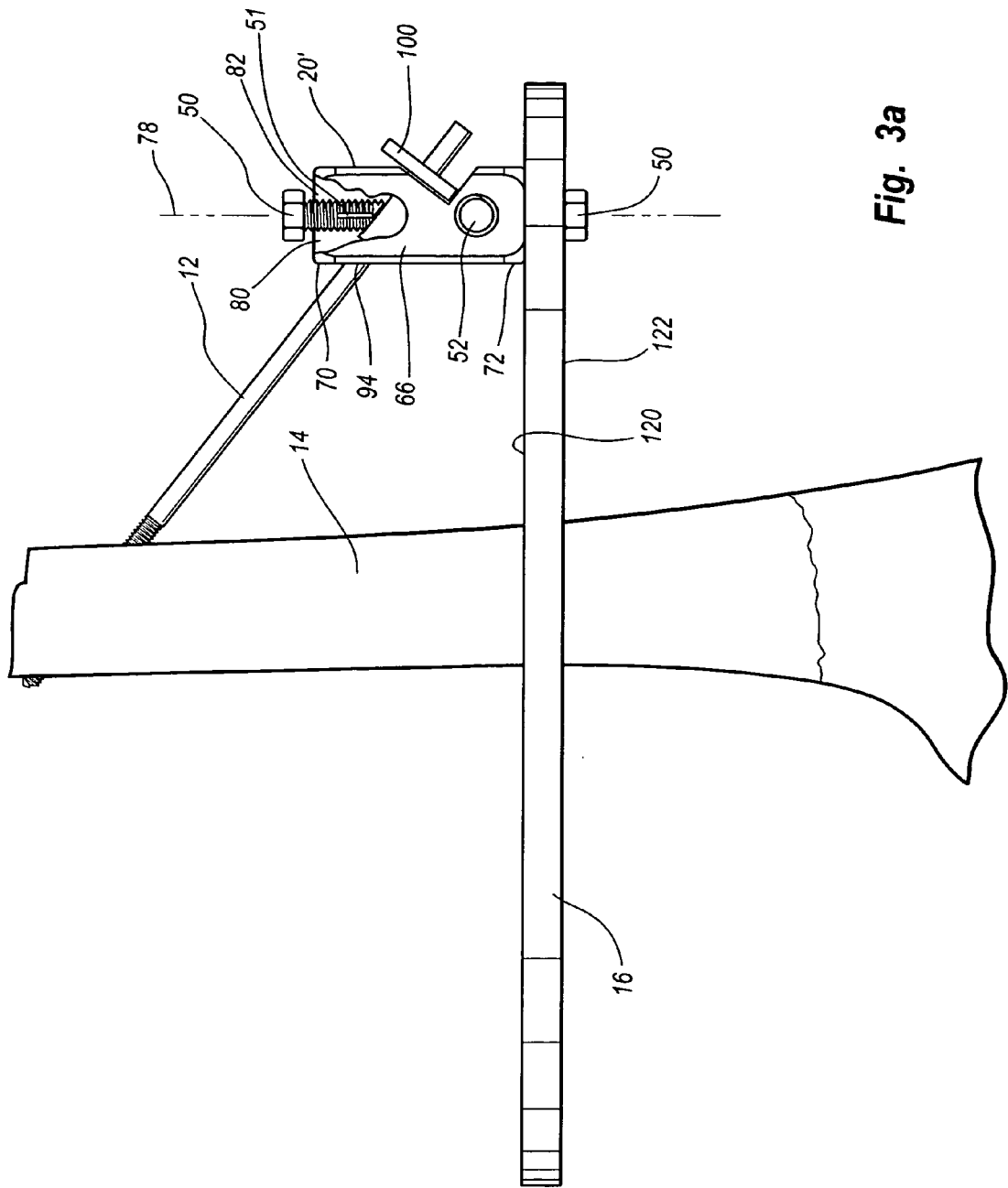
FIGS. 3a to 3d are elevated side views of four variations of system shown in FIG. 2b.

As also depicted in FIG. 2b, frame 16 comprises a substantially flat circular member 118 having a top surface 120 and an opposing bottom surface 122. A plurality of spaced part holes 46 extend through frame 16 between opposing surfaces 120 and 122. Frame 16 also has an interior surface 124 that bounds a central opening 126. During use, as depicted in FIG. 2a, the long bone to be fixed, such as a portion of an arm or leg, is passed through opening 126 so that frame 16 encircles the long bone. Fixing block 20' is secured to frame 16 by aligning first opening 82 or second opening 84 of mounting channel 80 with a hole 46 on one side of frame 16. A fastener 50, such as a bolt or screw, is passed through the corresponding hole 46 from the opposing side of frame 16 and threaded into mounting channel 80 so as to removably secure fixing block 20' to frame 16. In one embodiment fastener 50 comprises a stainless steel hex head Nylock bolt. As depicted in FIG. 3a, Nylock bolts typically have a slot 51 longitudinally extending along a length of the threaded shaft of the bolt. Slot 51 is filled with a plastic material, like nylon, such that as the bolt is threaded into a threaded hole, the threads in the corresponding hole engage the plastic material so as to help secure the bolt in place.

Here again it is noted that bone pin 12 extends at an orientation relative to top surface 120 and/or bottom surface 122 and/or the plane in which frame 16 is disposed at an angle β that is an oblique angle. The angle β is typically in a range between about 15° to about 75° with about 60° to about 30° being more common and about 50° to about 40° being still more common. Other angles can also be used.

It is appreciated that frame 16 can have a variety of different configurations. For example, frame 16 can have a substantially U- or C-shaped configuration or can comprise two or more parts secured together. Frame 16 can typically be comprised of a structure having sufficiently rigidity to securely hold the bone pins 12 at a desired location and for which a plurality of spaced apart fixing blocks 20' can be selectively attached.

In the present invention, bone pins 12 can comprise conventional half pins where distal end 12 is threaded for engagement with the bone and proximal end 12b has a smooth cylindrical configuration. Half pins typically have an extended length that is cut to a desired length after placement. In an alternative embodiment, bone pins 12 can comprise a cannulated drill pin that encircles a guide wire. Cannulated drill pins can be directly drilled into the bone by following the predrilled guide wire. Examples of cannulated drill pins with guide wire that can be used with the present invention are disclosed in U.S. patent application Ser. No. 11/198,637, filed Aug. 5, 2005 which is incorporated herein by specific reference.

Referring now to FIGS. 3a-3d, a variety of different configurations of bone stabilizing system 24 of the present invention are shown. FIG. 3a shows a configuration similar to the of FIG. 2a. However, in contrast to using fastener 116 to pass through access port 92 on fixing block 20' for securing bone pin 12, a fastener 50 is advanced down through first opening 82 of mounting channel 80 for engaging with bone pin 12 so as to secure bone pin 12 to fixing block 20'. As such, access port 92 can be eliminated from this embodiment. It has been found that using a bolt with polygonal head to secure bone pin 12 is substantially more convenient than using traditional set screws which can be small and difficult to operate. Furthermore, placing the bolt through the mounting channel 80 provides easier access to the fastener than using access port 92 on the side of fixing block 20'.

Furthermore, a second placement channel 52 is formed on fixing block 20' and extends between opposing sides 66 and 68. However, in contrast to placement channel 94 that extends at an oblique angle relative to central axis 78, second placement channel 52 extends normal to central axis 78. As such, by selectively rotating fixing block 20' by 90° on frame 16, fixing block 20' can be used for securing a bone pin 12 that connects with the bone 14 at a substantially orthogonal orientation or an oblique orientation. In an alternative embodiment, second placement channel 52 can also extend at an oblique angle relative to central axis 78 but at a different angle than placement channel 94. As such, the operator can selectively decide how to rotate fixing block 20' for the desired orientation of bone pin 12. In contrast or in addition to having second placement channel 52 extend between opposing sides 66 and 68, it is also appreciated that one or more additional placement channels can also extend between opposing faces 62 and 62 of fixing block 20' at an angle different than placement channel 94.

Figure 3B:
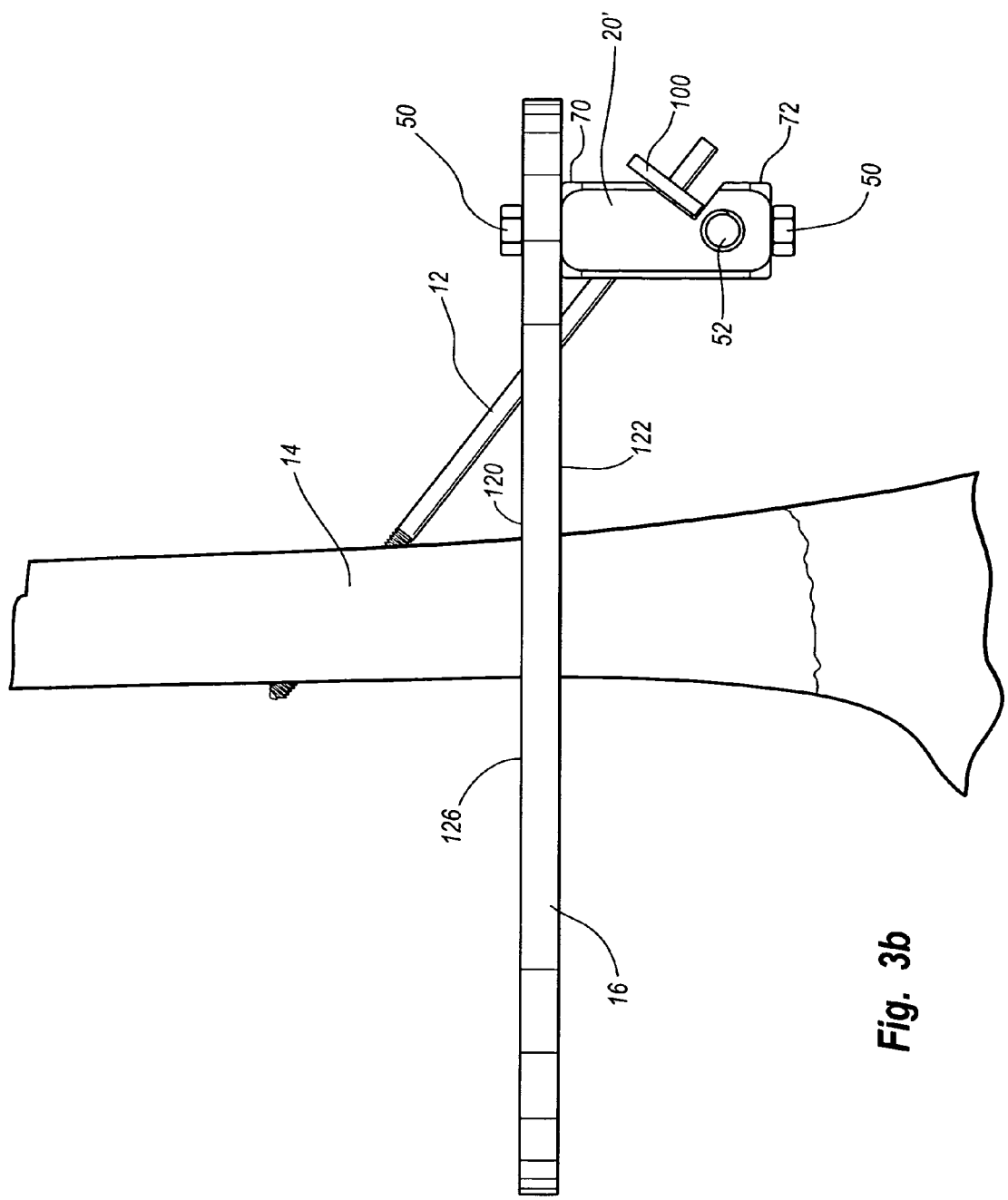
Figure 3C:
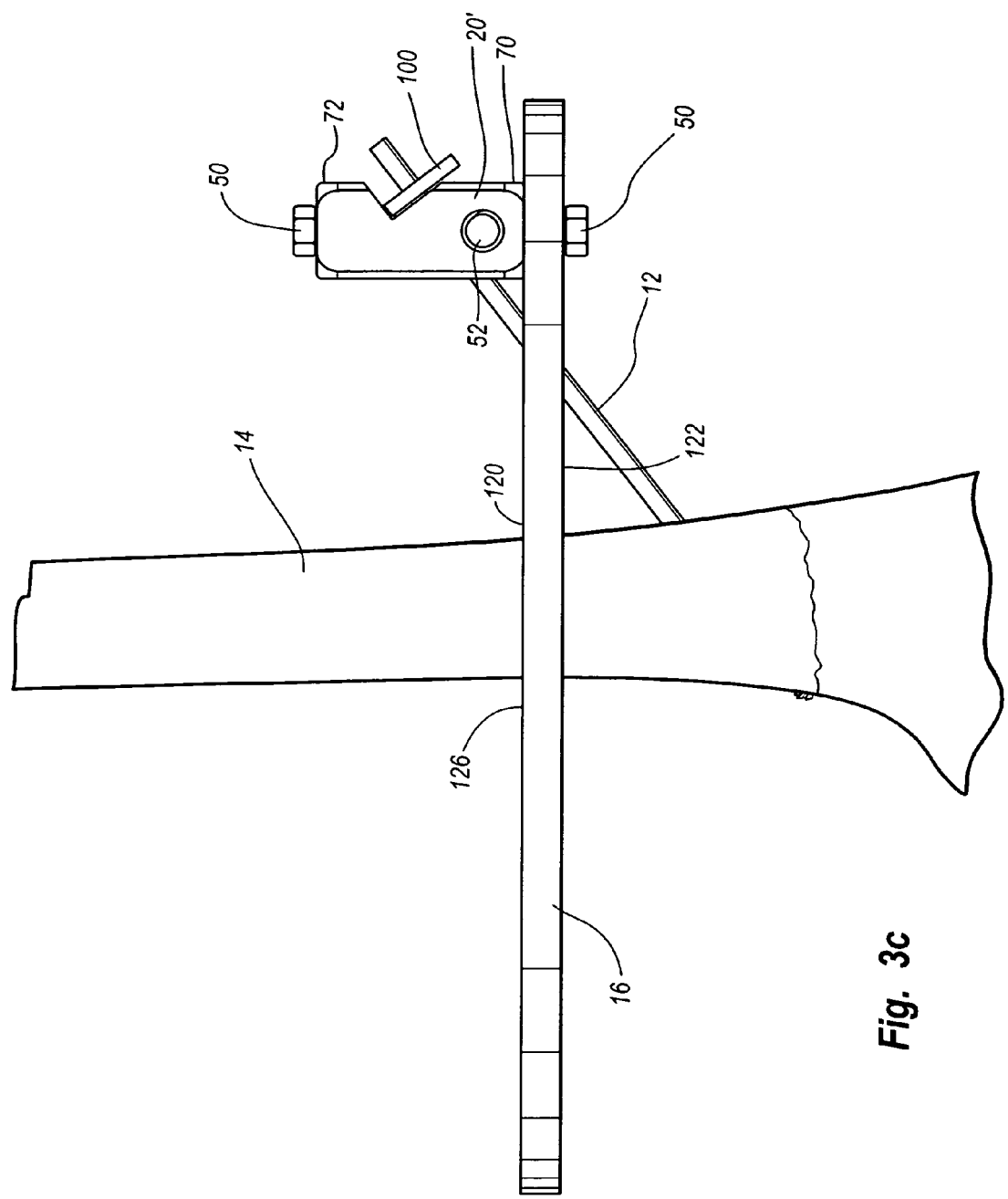
Figure 3D:
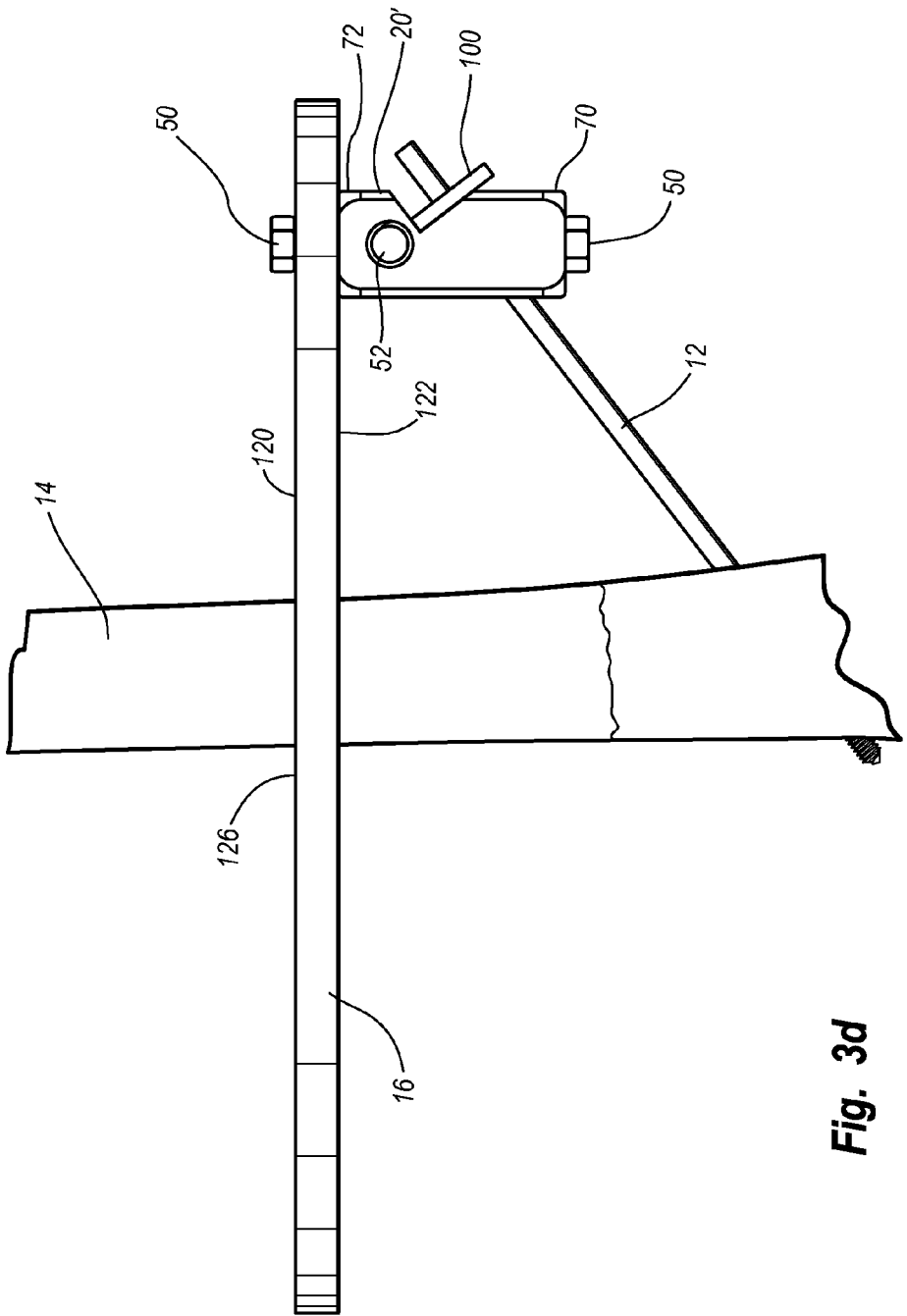

FIG. 3b shows first end 70 of fixing block 20' being secured to bottom surface 122 of frame 16. In this configuration, bone pin 12 passes up through opening 126 in frame 16. In FIG. 3c, fixing block 20' has been inverted relative to FIG. 3a so that first end 70 is secured to top surface 120 of frame 16 as opposed to second end 72 being secured to top surface 120. In this configuration, bone pin 12 passes down through opening 126 in frame 16. Finally, in FIG. 3d second end 72 of fixing block 20' is secured to bottom surface 122 of frame 16. In view of FIGS. 3a-3b, it is appreciated that fixing block 20' can be selectively inverted and/or attached to top surface 120 or bottom surface 122 of frame 16 so as to facilitate the desired placement and orientation of bone pin 12. Fixing block 20' can also be moved to any desired location along frame 16 and can be selectively rotated to use placement channel 52 or placement channel 94.

Figure 4:
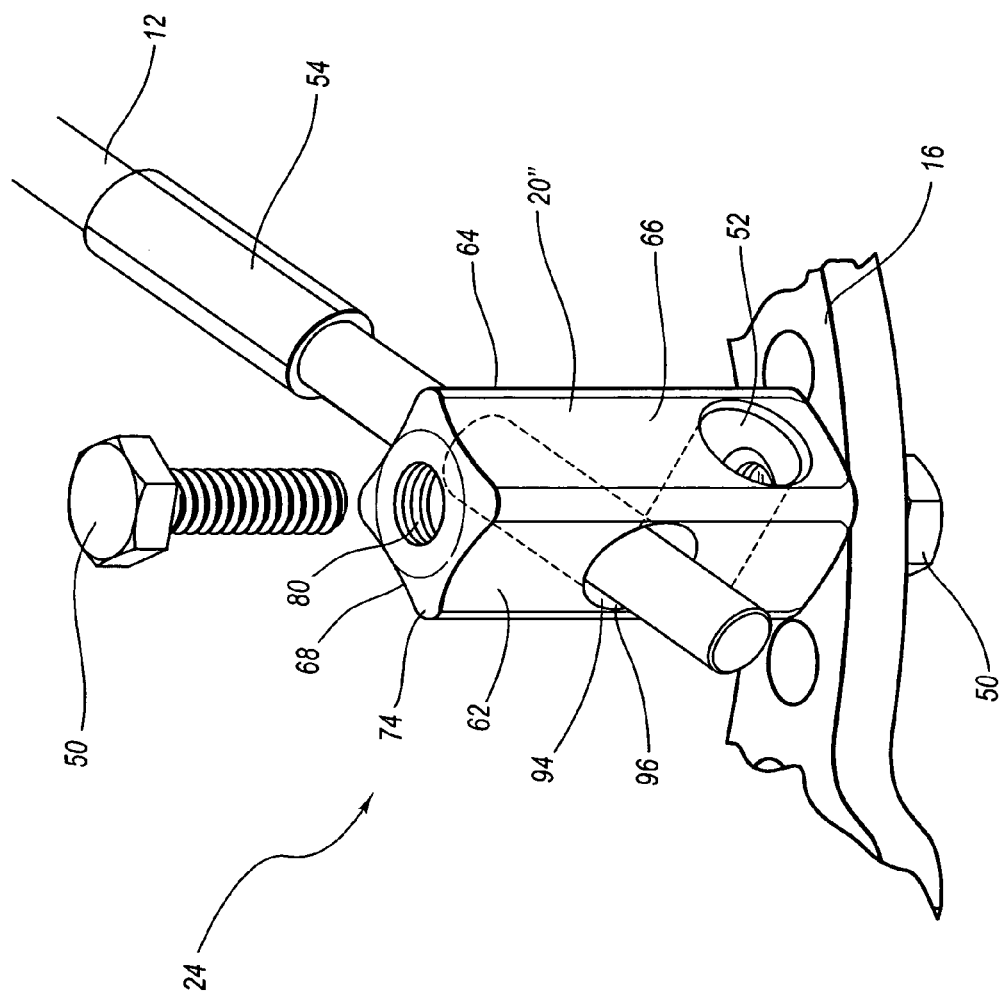
FIG. 4 is a perspective view of an alternative embodiment of the fixing block shown in FIG. 2b.

Depicted in FIG. 4 is another alternative embodiment of a fixing block 20" incorporating features of the present invention wherein like elements between fixing blocks 20' and 20" are identified by like reference characters. In contrast to fixing block 20' depicted in FIG. 2c, notch 86 and access port 92 have been eliminated. As such, placement channel 94 extend directly between front face 62 and opposing back face 64. Fastener 50 is threaded into mounting channel 80 so as to secure bone pin 12 within placement channel 94. In this embodiment, bone pin 12 can be secured to fixing block 20" with or without the use of guide sleeve 100. However, if desired, a tubular sleeve 54 can be selectively received into placement channel 94 to more accurately constrain the bone pin 12, or, optionally, to guide a drill when drilling into the bone 14.

Figure 5E:
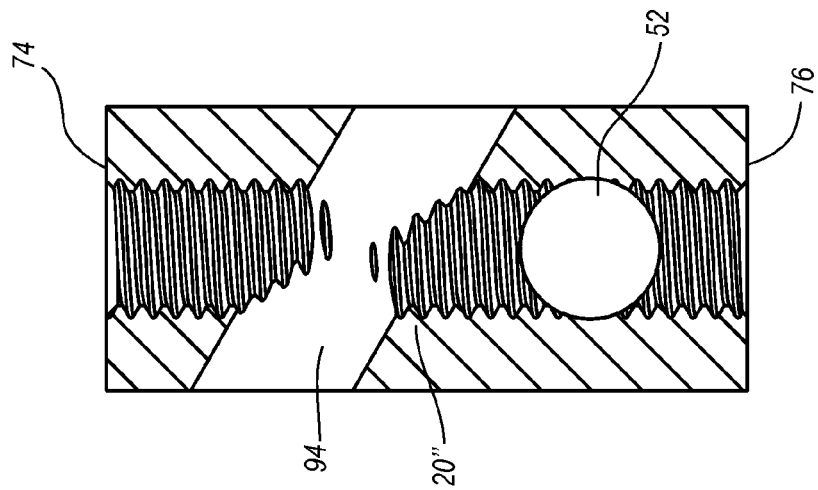
FIG. 5e is a cross section side view of the fixing block shown in FIG. 5c taken along section lines 5e-5e.
Figure 5D:
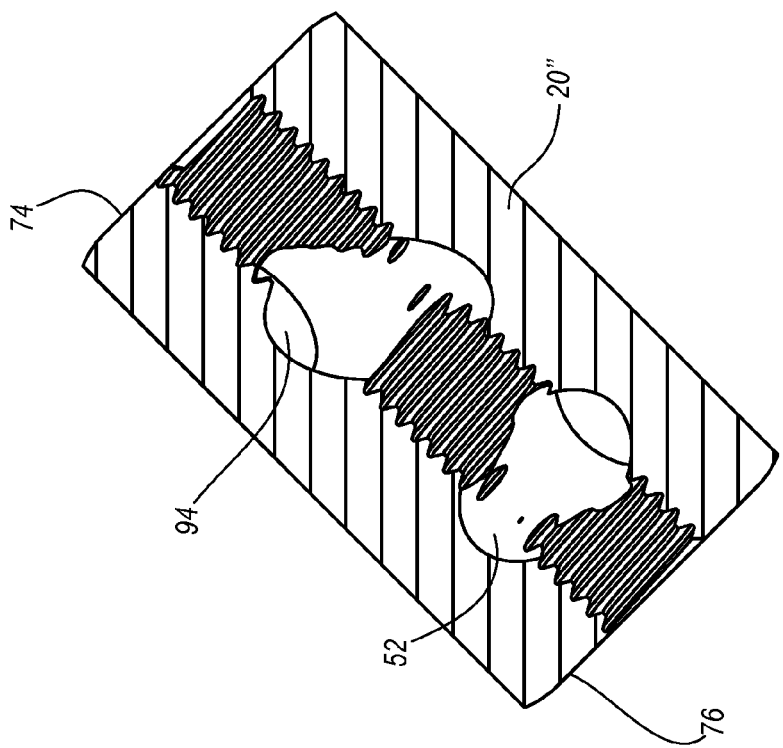
FIG. 5d is a cross section side view of the fixing block shown in FIG. 5c taken along section lines 5d-5d.

Depicted in FIGS. 5a-5e are alternative views of fixing block 20". For example, depicted in FIG. 5a is an elevated back side view. Here it is noted that because of the oblique orientation of placement channel 94, openings 96 and 98 of placement channel 94 have a substantially elliptical configuration. FIG. 5b is an elevated side view of fixing block 20" while FIG. 5c is a top plan view thereof. FIGS. 5d and 5e are cross sectional side views of fixing block 20" taken along the lines shown in FIG. 5c.

Figure 6:
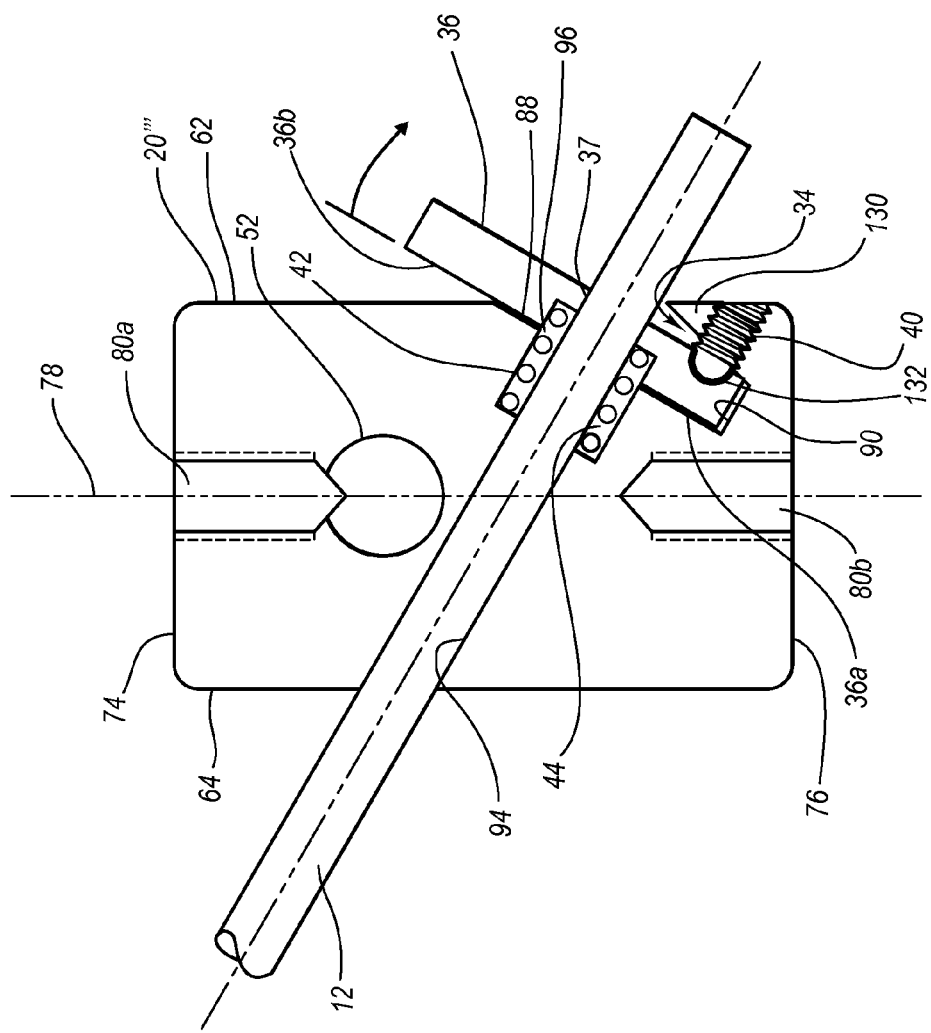
FIG. 6 is a cross sectional view of an alternative embodiment of a fixing block.

Depicted in FIG. 6 is an alternative embodiment of a fixing block 20''' wherein like elements between fixing blocks 20' and 20''' are identified by like reference characters. Fixing block 20''' includes a brace 130 upstanding from support face 90. As a result, a lower recess 34 is formed between brace 130 and engagement face 88. A first end 36a of a flat washer 36 is received within recess 34 so that washer 36 is disposed adjacent to engagement face 88. Washer 36 has a hole 37 extending therethrough that is aligned with placement channel 94. Brace 130 slopes away from engagement face 88 so that an opposing second end 36b of washer 36 can pivot toward and away from engagement face 88. Although not required, a set screw 40 or other fastener can be advanced through brace 130 so as to engage a indent 132 formed on washer 36, thereby securing washer 36 within recess 34.

An annular cavity 44 is formed on fixing block 20''' so as to encircle placement channel 94 adjacent to first opening 96. A spring 42 is disposed within cavity 44 and is compressed between fixing block 20''' and washer 36. It is appreciated that spring 42 can comprise a coiled spring or any other resilient member or material that can produce a resilient force against washer 36.

During use, bone pin 12 extends through placement channel 94 and hole 37 in washer 36. Spring 42 produces a resilient force against washer 36 that urges second end 36b of washer 36 to move away from engagement face 88 which in turn causes washer 36 to wedge or jam against bone pin 12, thereby securing bone pin 12 in place. By manually pressing second end 36b of the washer 36 back up against or toward engagement face 88 (against the bias of spring 42), causes bone pin 12 to become unjammed or unlocked, permitting bone pin 12 to freely slide through washer 36 and placement channel 94.

In contrast to fixing block 20' that includes mounting channel 80 that extends completely through fixing block 20' between opposing end faces 74 and 76, fixing block 20''' includes separate mounting channels 80a and 80b in the form of blind sockets formed on end faces 74 and 76, respectively.

Figure 7A:
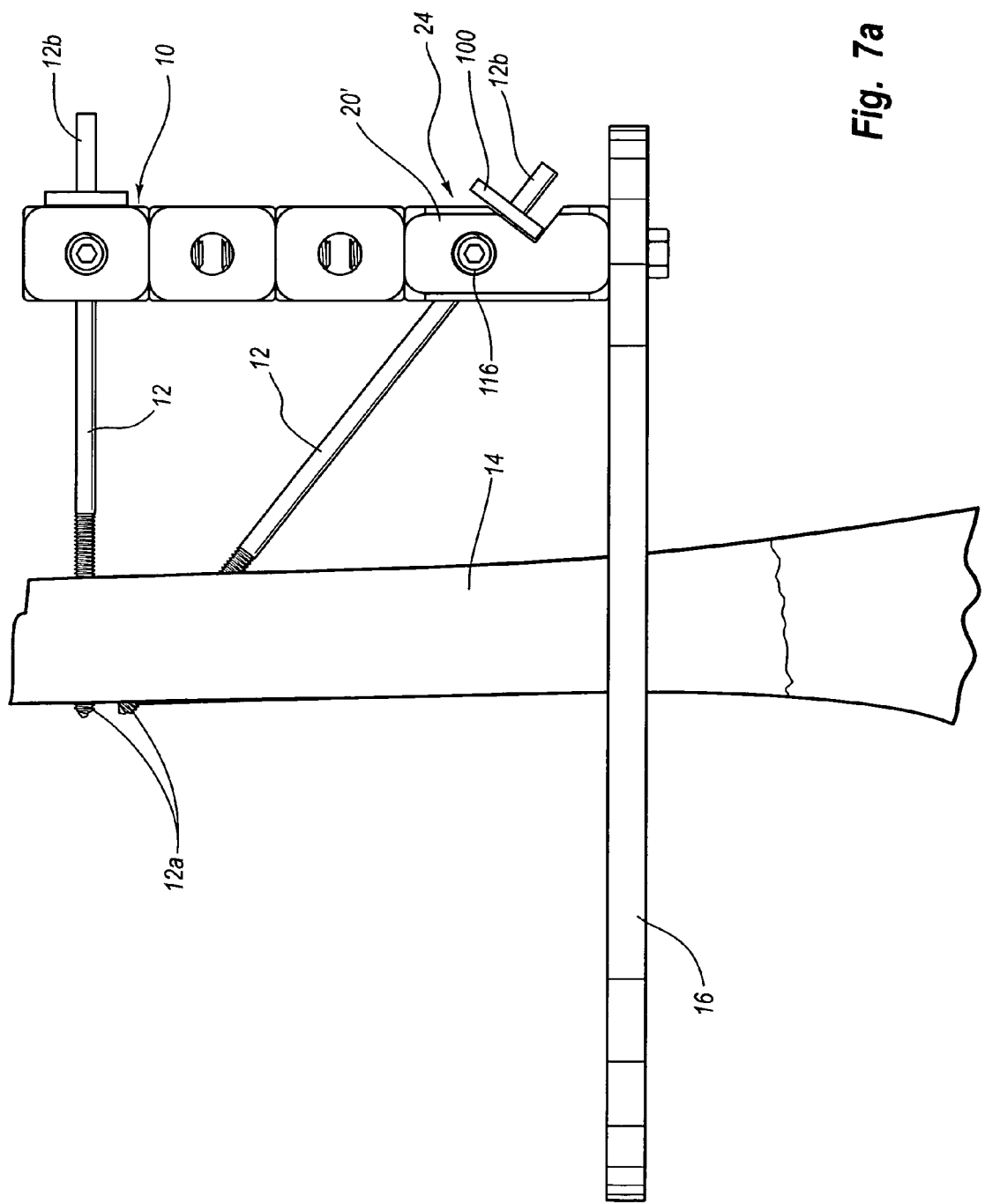
FIG. 7a is an elevated side view of a stacked assembly of fixing blocks mounted on a frame.

Referring now to FIG. 7a, a combination of a prior art system 10 and the system 24 of the present invention is shown, further demonstrating the adaptability of the invention. Specifically, any combination of fixing blocks 20 and/or fixing blocks 20', 20", 20''' can be vertically mounted or stacked together on frame 16 to provide further variations in the structure built to support bone 14. For example, the fixing blocks can be stacked so as to enable a single bone pin 12 to be fixed at a location spaced apart from frame 16. In yet other embodiments, the fixing block can be stacked so that two or more bone pins 12 can be mounted to the stacked fixing blocks so as to optimize bone pin placement and orientation.

Figure 7B:
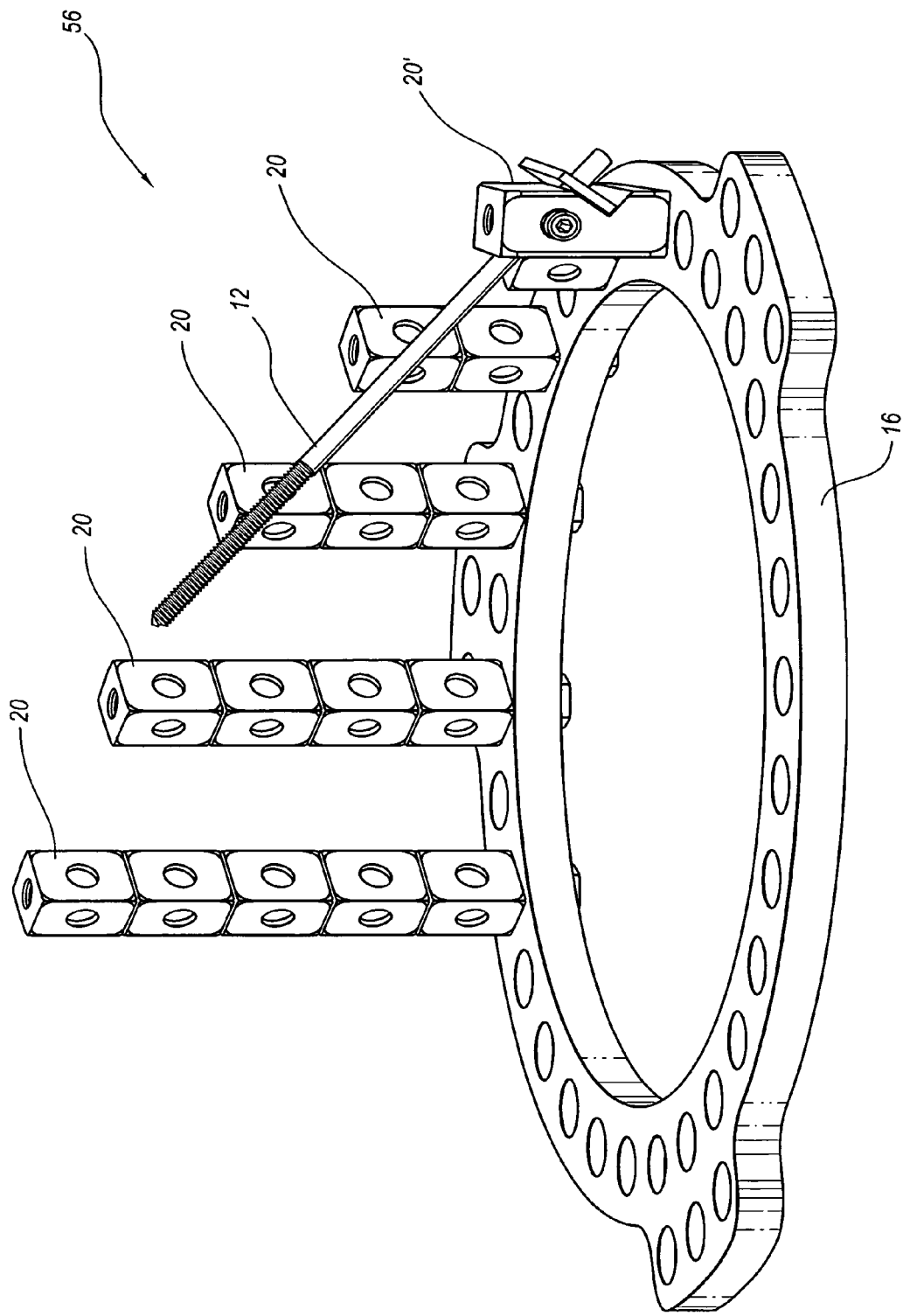
FIG. 7b is an elevated side view of a plurality of stacked assemblies of fixing blocks mounted on the frame.

Referring now to FIG. 7b, an exemplary setup 56 includes a frame 16 on which a variety of fixing blocks 20, 20' of varying heights are attached, together with one drill pin 12, attached obliquely to fixing block 20'. It is again appreciated that any number or combination of fixing blocks can be used on frame 16 with any desired combination of bone pins 12 to facilitate optimal bone stabilization.

Figure 8:
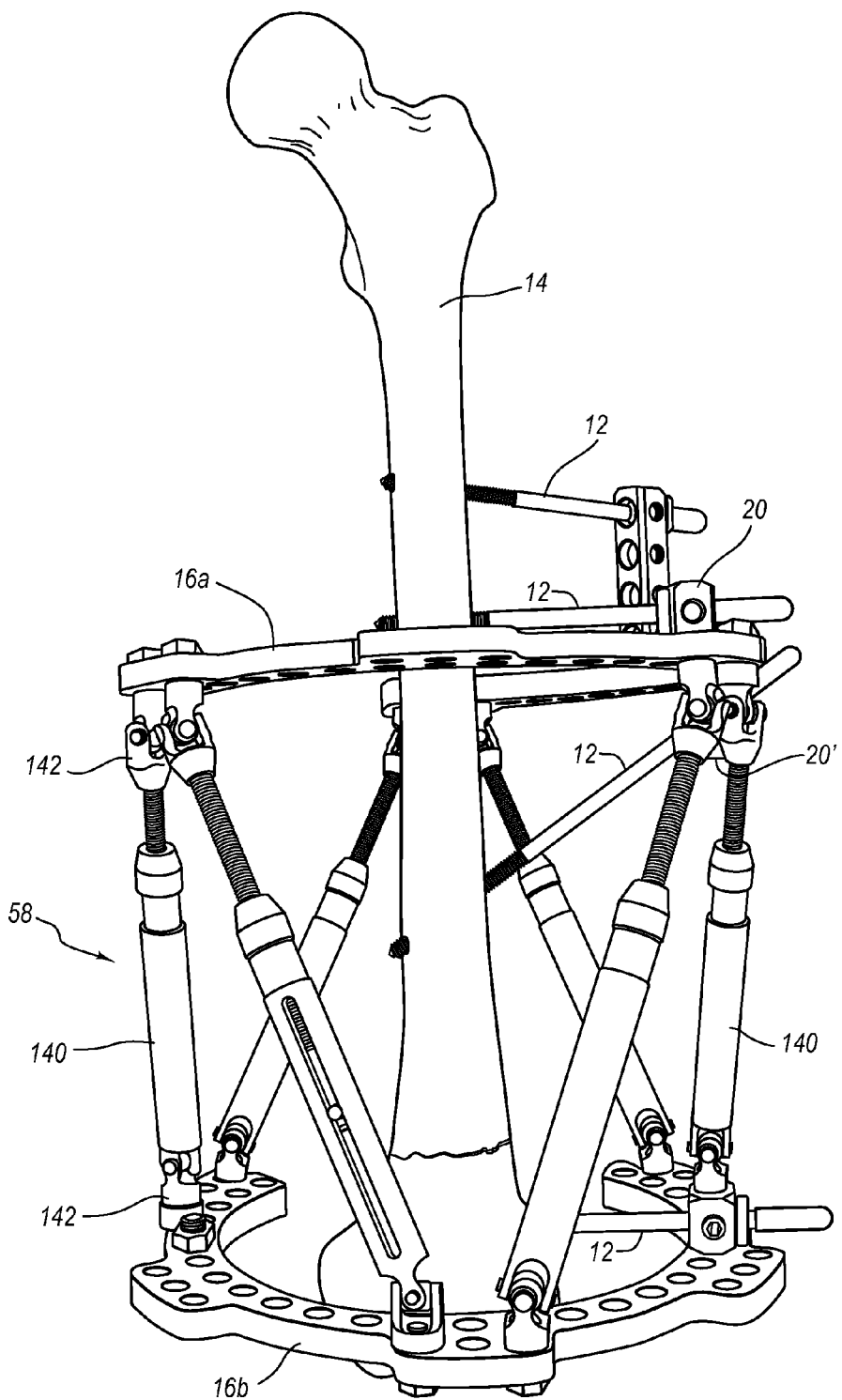
FIG. 8 is a perspective view of an external fixator attached to a femur showing one system of the invention configured in a manner to stabilize a bone.

Depicted in FIG. 8 is an external fixator assembly 58 incorporating features of the present invention and being used to stabilize a fractured femur 14. Fixator assembly 58 includes a first frame 16a and a spaced apart second frame 16b. A plurality of arms 140 extend between frames 16a and 16b. Each arm 140 is longitudinally adjustable. Furthermore, each end of each arm 140 is hingedly mounted to frame 16a and 16b by a universal joint 142. Various fixing blocks 20 and 20' are mounted to frame 16a and 16b so that a plurality of bone pins 12 can extend from the fixing blocks to the femur 14 so as to stabilize femur 14. It is noted that in this embodiment each frame 16a and 16b has a substantially C-shaped configuration.

It is appreciated that a variety of different methods can be implemented when using the bone stabilizing systems of the present invention. In one method, the bone 14 is drilled, optionally using a sleeve 54 affixed to the system 24 of the invention. Once bone 14 is drilled, the drill is removed. In a third step, one end of a bone pin 12 is inserted into bone 14 non-orthogonally with respect to the bone surface. In a fourth step, an opposite end of the bone pin 12 is inserted into a fixing block, such as those disclosed herein and non-orthogonally with respect thereto. In a fifth step, the fixing block is fixed to the frame 16. In a sixth step, further fixing blocks may be fastened to the frame 16 in order to stabilize the bone 14 within the frame to promote proper healing and setting of the bone in a desired orientation. In alternative embodiments, various steps can be switched or eliminated. For example, where the cannulated drill pin is used, the drill pin can be drilled into the bone by following the previously drilled guide wire. The guide wire is removed after mounting of the drill pin.

In an advantage, the invention permits insertion of bone pins 12 at a fixed angle relative to the bone, thus resulting in increased bone purchase. Because of the angled trajectory of the pin, the strength of fixation is superior to that of standard transverse pins and clamps. More bone may be gripped from a given fixator ring, adding to the stability of the final construct.

In an advantage, the obliquely placed pins cover more territory of bone per pin, as thereby increasing the strength of fixation.

In another advantage, the increased pin/fixing block interface provides more rigid fixation of the bone pin 12.

In another advantage, many possible mounting configurations per pin 12 offer wide versatility in bone fixation choices.

In another advantage, the invention increases the strength of fixation of the bone 14 while streamlining the frame construct and making it lighter. That is, the relatively low profile device provides a secure and lightweight method of attaching bone pins to the frame.

In another advantage, because the fixing blocks are secured directly to the frame rings, without the need to build up transitional attachments, the overall frame construct is lighter and stronger due to the buttress effect of the oblique pins (triangles are stronger than rectangles).

Multiple variations and modifications are possible in the embodiments of the invention described here. Although certain illustrative embodiments of the invention have been shown and described here a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A bone fixation system comprising:
    a fixing block comprising:
        a body having an opposing front and back face and also an opposing first and second side face each extending between a first end face and an opposing second end face, a mounting channel extending through the body between the first end face and the opposing second end face, a first placement channel extending through the body between the front face and the back face, the first placement channel being formed through the body so as to intersect with the mounting channel at a fixed first oblique angle, the first placement channel being adapted to receive a bone pin;
    a first fastener threaded into the mounting channel at the first end face of the body; and
    a second fastener threaded into the mounting channel at the second end face of the body, the second fastener being separate and distinct from the first fastener;
    an elongated bone pin having a threaded portion for engaging bone, the bone pin being slidably positioned within the first placement channel, the second fastener pressing against the bone pin; and
    a frame having an opening configured to pass a portion of an arm or a leg therethrough, the first fastener securing the fixing block to the frame.

2. The bone fixation system as recited in claim 1, further comprising a second placement channel extending through the body between the first side face and the second side face, the second placement channel being unthreaded and intersecting with the mounting channel.

3. The bone fixation system as recited in claim 2, wherein the second placement channel intersects with the mounting channel at an orthogonal angle.

4. The bone fixation system as recited in claim 2, wherein the second placement channel intersects with the mounting channel at a fixed second oblique angle that is different than the fixed first oblique angle.

5. The bone fixation system as recited in claim 1, further comprising a second placement channel extending through the body between the front face and the back face, the second placement channel intersecting with the mounting channel.

6. The bone fixation system as recited in claim 1, wherein the front face and the back face or the first side face and the second side face are each substantially planar and are disposed in substantially parallel alignment.

7. The bone fixation system as recited in claim 1, wherein the second fastener comprises a bolt having an enlarged polygonal head, a threaded shaft projecting from the head, a slot longitudinally recessed along at least a portion of the threaded shaft, and a polymeric material disposed within the slot.

8. The bone fixation system as recited in claim 1, wherein the front face of the body is notched so that an engagement face intersects with the first placement channel at a substantially orthogonal angle.

9. The bone fixation system as recited in claim 8, further comprising a guide sleeve, the guide sleeve including a tubular stem and an enlarged head mounted on the end thereof, a passage longitudinally extending through the stem and through the head, a transition port transversely extending through the stem so as to communicate with the passage, the stem being received within the first placement channel so that the head thereof is disposed against or adjacent to the engagement face of the body.

10. The bone fixation system as recited in claim 9, wherein the transition port of the guide sleeve is aligned with the mounting channel so that the second fastener can selectively advance into the transition port of the guide sleeve.

11. The bone fixation system as recited in claim 1, wherein the body includes a flat engagement face lying perpendicular to the axis of the bone pin passing through the first placement channel, the engagement face being adjacent to a recess which receives an end of a flat washer so as to constrain the end of the washer, a spring being interposed between the body and the flat washer to urge the flat washer away from the engagement face, so that, when a pin passes through the washer and first placement channel, the flat washer jams the pin in place.

12. The bone fixation system as recited in claim 11, wherein when an opposite end of the flat washer is depressed against the bias of the spring so that the flat washer bears against the engagement face, the pin is released from being jammed against movement.

13. The bone fixation system as recited in claim 1, wherein the first oblique angle is in a range between about 30° to about 60°.

14. The bone fixation system as recited in claim 1, wherein the first oblique angle is in a range between about 40° to about 50°.

15. The bone fixation system as recited in claim 1, further comprising:
the first placement channel of the fixing block having a central longitudinal axis that intersects with the mounting channel of the fixing block at a fixed oblique angle; and
the frame is disposed within a plane, the fixing block being secured to the frame so that the central longitudinal axis of the first placement channel intersects with the plane of the frame at an oblique angle.

16. The bone fixation system as recited in claim 15, wherein the opening of the frame has a central longitudinal axis, the plane of the frame extending through the opening of the frame so that the central longitudinal axis of the opening is perpendicular to the plane.

17. The bone fixation system as recited in claim 1, further comprising:
the first placement channel of the fixing block having a central longitudinal axis that intersects with the mounting channel of the fixing block at a fixed oblique angle; and
the frame having a first side face and an opposing second side face with the opening extending therebetween, the first side face being planar and disposed within a plane, the fixing block being secured to the frame so that the central longitudinal axis of the first placement channel intersects with the plane of the frame at a fixed oblique angle.

18. A system for stabilizing bone, the system comprising:
a fixing block having an encircling side face extending between a first end face and an opposing second end face, an axis centrally extending through the first end face and the second end face, a first placement channel having a cylindrical configuration and being formed through the fixing block so as to pass through the encircling side face and intersect with the axis at a fixed first oblique angle;
a frame removably coupled with the fixing block; an elongated bone pin having a threaded portion adapted for engaging bone, the bone pin being slidably positioned within the first placement channel so that an elongated axis of the bone pin is disposed at a fixed oblique angle to the axis of the fixing block; a mounting channel extending from the second end face of the fixing block to the first placement channel, at least a portion of the mounting channel being threaded; and a fastener comprising a bolt having an enlarged polygonal head, a threaded shaft projecting from the head, the fastener being threaded into the mounting channel so that the fastener biases against the bone pin, thereby securing the bone pin in place.

19. The system as recited in claim 18, further comprising a first fastener securing the bone pin to the fixing block.

20. The system as recited in claim 18, further comprising a second placement channel extending through the fixing block, the second placement channel intersecting with the axis of the fixing block at an angle different than the first oblique angle.

21. The system as recited in claim 18, wherein the side face of the fixing block is notched so that an engagement surface intersects with the first placement channel at a substantially orthogonal angle.

22. The system as recited in claim 21, further comprising a guide sleeve, the guide sleeve including a tubular stem and an enlarged head mounted on the end thereof, a first passage longitudinally extending through the stem and through the head, a transition port transversely extending through the stem, the stem being received within the first placement channel so that the head is disposed against or adjacent to the engagement surface of the fixing block.

23. The system as recited in claim 22, wherein the transition port of the guide sleeve is aligned with the mounting channel so that a second fastener can selectively advance into the transition port of the guide sleeve.

24. The system as recited in claim 18, further comprising:
the first placement channel of the fixing block having a central longitudinal axis that intersects with the axis extending through the opposing end faces of the fixing block at a fixed oblique angle; and
the frame is disposed within a plane, the fixing block being coupled to the frame so that the central longitudinal axis of the first placement channel intersects with the plane of the frame at a fixed oblique angle.

25. The system as recited in claim 24, wherein the frame has a first side face and an opposing second side face with the opening extending therebetween, opening having a central longitudinal axis, the plane of the frame extending through the opening of the frame so that the central longitudinal axis of the opening is perpendicular to the plane.

26. A bone fixation system comprising:
a fixing block comprising:
a body having an opposing front and back face and also an opposing first and second side face each extending between a first end face and an opposing second end face, a mounting channel extending through the body between the first end face and the opposing second end face, a first placement channel extending through the body between the front face and the back face, the first placement channel intersecting with the mounting channel at a fixed oblique angle, a second placement channel extending through the body between the first side face and the second side face, the second placement channel intersecting orthogonally with the mounting channel;
a first fastener threaded into the mounting channel at the first end face of the body;
an elongated bone pin having a threaded portion for engaging bone, the bone pin being slidably positioned within the first placement channel;
a second fastener threaded into the mounting channel at the first end face of the body, the second fastener biasing against the bone pin;
a first frame having a ring shaped or C-shaped configuration with an inside edge that bounds an opening configured to receive a portion of an arm or a leg therein, the first fastener securing the fixing block to the first frame;
a second frame having a ring shaped or C-shaped configuration with an inside edge that bounds an opening configured to receive a portion of an arm or a leg therein; and
a plurality of elongated arms extending from the first frame to the second frame.

* * * * *

UNITED STATES PATENT AND TRADEMARK OFFICE
CERTIFICATE OF CORRECTION

PATENT NO.         : 8,469,958 B2                                                                Page 1 of 1
APPLICATION NO.    : 11/346924
DATED              : June 25, 2013
INVENTOR(S)        : Stevens It is certified that error appears in the above-identified patent and that said Letters Patent is hereby corrected as shown below:

In the Specification

Column 4
Line 29, change "spaced part holes" to --spaced apart holes--
Line 46, change "threaded hole, the threads" to --threaded hole. The threads--
Line 65, change "distal end 12" to --distal end 12*a*--

Column 5
Line 12, change "similar to the of" to --similar to that of--
Line 42, change "62 and 62" to --62 and 64--
Line 65, change "extend" to --extends--

Column 6
Line 31, change "engage a indent" to --engage an indent--
Line 44, change "By manually" to --Manually--

Column 7
Line 16, change "frame 16*a* and 16*b*" to --frames 16*a* and 16*b*--

Column 8
Line 1, change "substitutions is contemplated" to --substitutions are contemplated--

Signed and Sealed this
Twentieth Day of January, 2015

Michelle K. Lee
*Deputy Director of the United States Patent and Trademark Office*